(12) United States Patent
Dhurjaty

(10) Patent No.: US 9,683,954 B2
(45) Date of Patent: Jun. 20, 2017

(54) SYSTEM AND METHOD FOR NON-CONTACT ASSESSMENT OF CHANGES IN CRITICAL MATERIAL PROPERTIES

(71) Applicant: Sreeram Dhurjaty, Rochester, NY (US)

(72) Inventor: Sreeram Dhurjaty, Rochester, NY (US)

( * ) Notice: Subject to any disclaimer, the term of this patent is extended or adjusted under 35 U.S.C. 154(b) by 611 days.

(21) Appl. No.: 14/165,502

(22) Filed: Jan. 27, 2014

(65) Prior Publication Data

US 2015/0212027 A1    Jul. 30, 2015

(51) Int. Cl.
*G01N 27/416* (2006.01)
*G01R 31/00* (2006.01)
*G01N 29/04* (2006.01)
*G01N 27/02* (2006.01)
*G01N 33/15* (2006.01)

(52) U.S. Cl.
CPC ........... *G01N 27/026* (2013.01); *G01N 33/15* (2013.01)

(58) Field of Classification Search
CPC ............................. G01N 27/026; G01N 33/15
USPC ....................... 324/426, 649, 750.03; 73/799
See application file for complete search history.

(56) References Cited

U.S. PATENT DOCUMENTS

| | | | | |
|---|---|---|---|---|
| 5,952,820 A | * | 9/1999 | Thrasher | G01R 19/155 324/119 |
| 6,511,851 B1 | * | 1/2003 | Payne | G01N 27/023 436/149 |
| 6,964,202 B2 | * | 11/2005 | Buttle | G01N 3/32 73/799 |
| 2003/0206021 A1 | * | 11/2003 | Laletin | G01R 31/3631 324/426 |
| 2013/0000402 A1 | * | 1/2013 | Bettacchioli | G01N 5/04 73/32 A |
| 2013/0181733 A1 | * | 7/2013 | Kikuchi | G01R 1/0466 324/750.03 |

\* cited by examiner

*Primary Examiner* — Farhana Hoque
(74) *Attorney, Agent, or Firm* — Patent Technologies, LLC; Robert D. Gunderman, Jr.

(57) ABSTRACT

A material signature detector that provides for the assessment of changes in critical material properties of materials such as pharmaceuticals and solutions is disclosed. The material signature detector is non-contact and non-invasive and provides the ability to detect unintended changes in the contents of a vial or other container during the fill-finish process, transport, compounding, or storage. The material signature detector uses a novel resonant electrical impulse spectroscopy circuit that employs quadrature demodulation at lower frequencies to detect changes in the capacitance and conductance (resistance) of the sample under test. A series of digital signatures are created at different frequencies to provide an overall assessment of changes in the properties of the material under test. These digital signatures may in turn be stored in an electronic library for subsequent analytics.

13 Claims, 11 Drawing Sheets

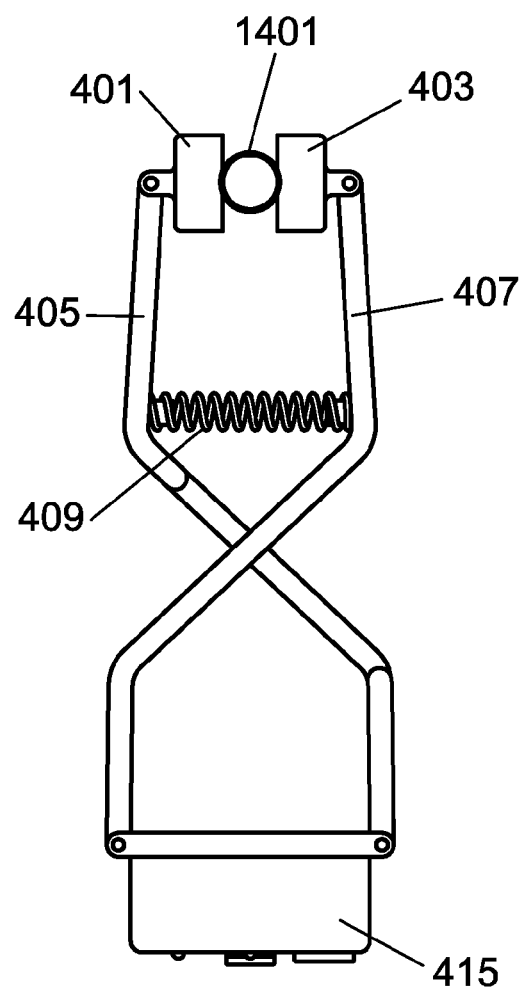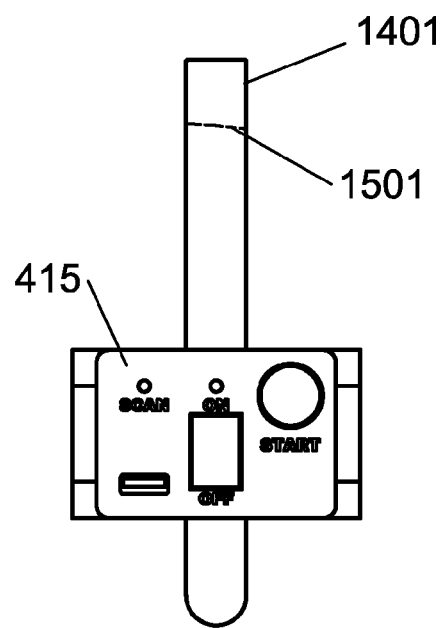
Fig. 14                    Fig. 15

SYSTEM AND METHOD FOR NON-CONTACT ASSESSMENT OF CHANGES IN CRITICAL MATERIAL PROPERTIES

BACKGROUND OF THE INVENTION

1. Field of the Invention

This invention relates generally to spectroscopy, and more particularly to a system and method for non-contact assessment of changes in critical material properties using a novel lower frequency dielectric absorption spectroscopy system and method.

2. Description of Related Art

Various liquids, solutions, and materials, such as pharmaceuticals, may undergo unintended changes during various steps such as the fill-finish process, transportation, compounding process, or storage. These changes may include changes in pH, salinity, or particulates and may, in the case of pharmaceuticals, be injurious to a patient's health. Compounding errors in solutions or pharmaceuticals prior to being administered may cause injury to the patient or even death. For example, errors in saline concentration in chemotherapy can represent a significant patient hazard. In addition, other substances such as expensive perfumes, gels and solid powders may be counterfeited, watered down, or otherwise made non-viable in an attempt to deceive the recipient of the counterfeit material. Such counterfeiting activities cause more than monetary harm, and may compromise the health and well-being of the recipient. The ability to determine the stability and authenticity of a material such as a pharmaceutical product without contacting or otherwise disturbing the material is a heretofore unmet need.

It would therefore be desirable to have the ability to detect unintended changes in the contents of a container such as a vial during various times such as the fill-finish process, transportation, the compounding process, or storage prior to infusion so that preventive or remedial actions could be taken. Detecting these unintended changes would benefit from being non-contact and non-invasive. Detecting variations in the contents of a container outside of pre-determined acceptable parameters would have vast implications in many industries, including, for example, the pharmaceutical industry.

While dielectric spectroscopy is used to determine the characteristics of various materials, it inherently uses extremely high frequencies approaching microwave frequencies, and therefore requires contact with the material since at these frequencies the glass or plastic container impedes these microwave signals and also can cause radiation of these signals into the environment.

What is needed, therefore, is a technique that determines the stability, authenticity and overall integrity of a material such as a liquid without the need to disrupt, remove, or otherwise disturb the packaging, container, or vial that contains the material.

The present invention employs a novel method of non-contact assessment of materials contained in a package, container, vial, vessel, or the like. While the various embodiments of the present invention are described as evaluating or analyzing materials such as pharmaceuticals that are contained in a vial or the like, other applications such as the analysis of a liquid such as blood, within a vessel of the body of a human or animal, are also considered within the scope and content of the present invention.

It is therefore an object of the present invention to provide a non-invasive and non-contact system and method for assessment of changes in critical material properties.

BRIEF SUMMARY OF THE INVENTION

In accordance with the present invention, there is provided a material signature detector for non-contact assessment of changes in critical material properties comprising an electrical circuit comprising a sense resistor in series with both an element and a sample under test; a frequency source electrically coupled between the sense resistor and a ground return; a quadrature demodulator electrically coupled in parallel with the sense resistor; and an analog to digital converter to create digital signatures from analog signals received from the quadrature demodulator.

The foregoing paragraph has been provided by way of introduction, and is not intended to limit the scope of the invention as described by this specification and the attached drawings and claims.

BRIEF DESCRIPTION OF THE DRAWINGS

The invention will be described, by reference to the following drawings, in which like numerals refer to like elements, and in which:

FIG. 14 is a top plan view of the material signature detector of the present invention in use with a vial of material;

FIG. 15 is a front plan view of the material signature detector of the present invention in use with a vial of material.

Figure 1:
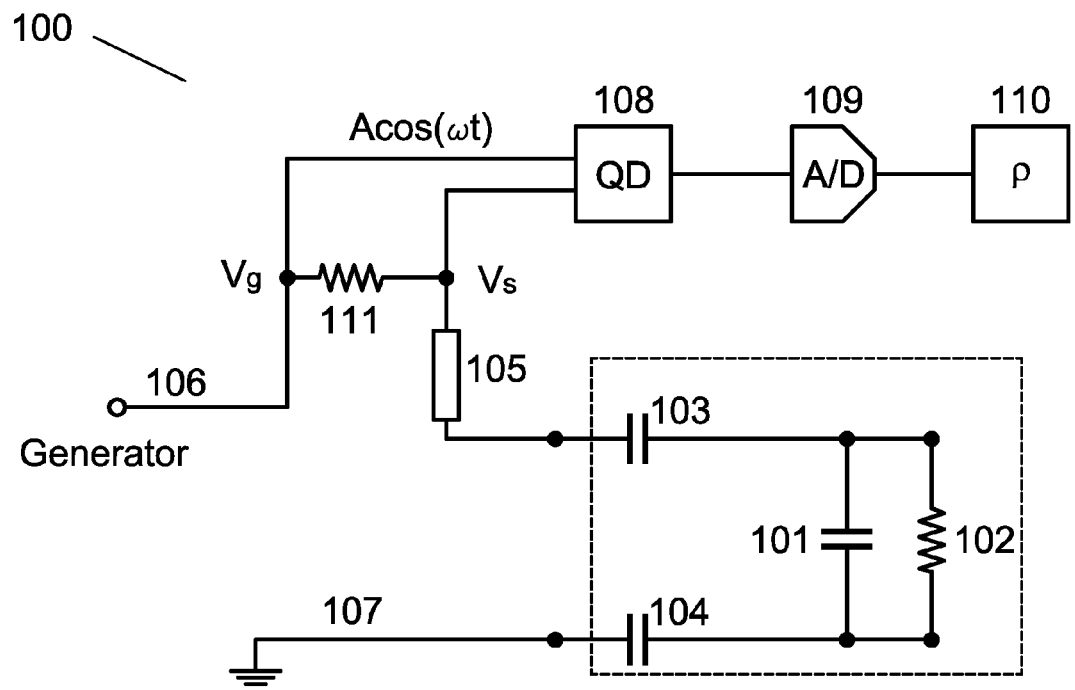
FIG. 1 is a schematic diagram of the material signature detector circuit of the present invention.

The present invention will be described in connection with a preferred embodiment, however, it will be understood that there is no intent to limit the invention to the embodiment described. On the contrary, the intent is to cover all alternatives, modifications, and equivalents as may be included within, the spirit and scope of the invention as defined by this specification, attached drawings and claims.

DESCRIPTION OF THE PREFERRED EMBODIMENTS

For a general understanding of the present invention, reference is made to the drawings. In the drawings, like reference numerals have been used throughout to designate identical elements.

The present invention will be described by way of example, and not limitation. Modifications, improvements and additions to the invention described herein may be determined after reading this specification and viewing the accompanying drawing such modifications, improvements, and additions being considered included in the spirit and broad scope of the present invention and its various embodiments described or envisioned herein.

The present invention, and the various embodiments described and envisioned herein, use a novel form of dielectric absorption spectroscopy performed at lower frequencies to allow for non-contact analysis of materials contained in a vial, vessel, package, or other container. At these lower frequencies detection of for example, changes in properties of polar and ionic molecules can be affected through the walls of a container. In addition, the permittivity of liquids is several orders of magnitude larger at lower frequencies than at traditional microwave frequencies. Therefore, the variation between signatures of corresponding changes in material properties is also large. Methods of the present invention create signatures for a particular material that define regions of stability. These signatures are then stored for later use. In some embodiments of the present invention, the signatures are stored in encrypted form. Using a device of the present invention, signatures are then collected to the material under test and compared to the stored signatures that define regions of stability. Variations between the stable signatures and the collected signatures can then be used as an indicator of authenticity and stability of the material.

The present invention monitors and detects changes in capacitance, conductance, and in some embodiments temperature, using sensors that reside entirely outside the container, vial, or infusing device.

Referring first to FIG. 1, there is illustrated a schematic diagram of the material signature detector circuit of the present invention.

An important premise of the present invention is that capacitance of a typical solution can be made up of a multitude of capacitances of various materials and can change due to temperature. In addition, the capacitance of a typical solution can change when excited by different frequencies. This is due in part to the presence of polar molecules and the molecular weights of each, factors that in turn determine the change in dielectric constant at various frequencies. In addition to capacitance of the solution, the resistivity of the solution may also change due to factors such as temperature, salinity, concentrations of polar or non-polar molecules, and the like. Based on these observations and the fact that a solution in a container such as a vial has a capacitive component and a resistive component, the contents of the container may be therefore modeled as a sample under test capacitance 101 in parallel with a sample under test resistance 102. The capacitance of the container itself may be modeled by capacitors 103 and 104 by virtue of the capacitive elements that connect the container to electrical signals used by the present invention. 105 is an element, in various embodiments, representing a combination of components such as inductors, resistors or active components, whose output, at the junction of 111 and 105, as a response to the frequencies and amplitudes of generator 106, changes with variations in components 101, 102, 103 and 104 (the constituent electrical components of the container and solution under test). 107 represents a reference ground for all measured electrical signals. In one embodiment, 111 represents a sense resistor that allows for the monitoring of changing voltages with respect to the function generator 106 as a response to changes in the material properties of the solution.

In one embodiment of the present invention, the resultant signals that are returned from the container and solution under test appear between the junction of the sense resistor 111 and element 105 and can be demodulated using phase sensitive techniques or using a lock-in-amplifier. In one embodiment of the present invention, the output and signal from the function generator 106, in one example being a cosine wave, are fed to a quadrature demodulator 108. The quadrature demodulator 108 uses the in phase signal A Cos($\omega$t) to generate a quadrature signal A Sin($\omega$t), and these are in turn used to generate amplitude and phase information after the output is subtracted from the signal produced by the function generator 106. In another embodiment of the present invention, the latter signal A Sin($\omega$t) is also generated at the function generator 106 and is fed to the quadrature demodulator 108. Quadrature demodulators are well known and serve to shift a signal by 90 degrees at the center frequency. The resulting signals are digitized by a multichannel A/D converter 109 and processed by the processor 110 to provide amplitude and phase information.

Figure 2:
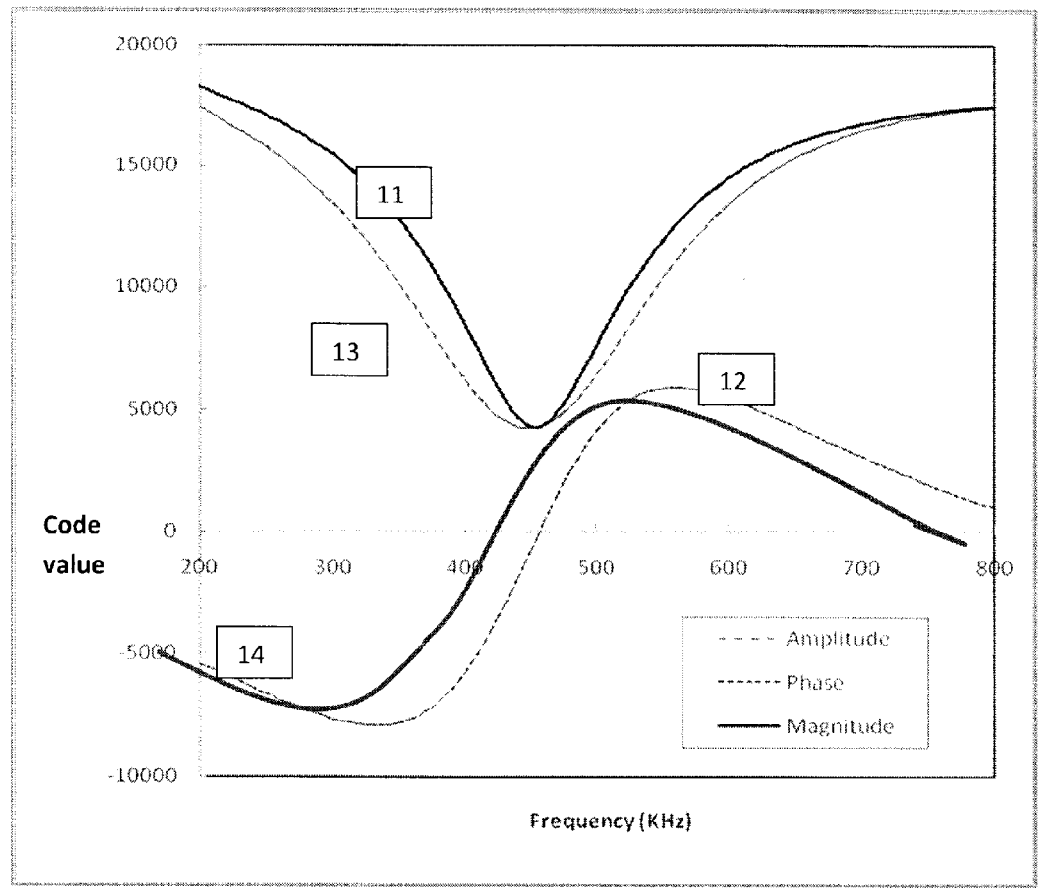
FIG. 2 is a graph depicting an example of behavior of the system of the present invention.

Now assume that the system is configured so that the sample under test capacitance 101 and the sample under test resistance 102 are in the configuration of a resonant circuit with the element 105 representing an inductor. FIG. 2 is a graph depicting an example of behavior of the system of the present invention and depicts some of the signals that are obtained from this embodiment, where 11 represents initial amplitude information and 12 the initial phase information which is the calibrated amplitude signature when the material is packaged in the factory or is the template signature for a certain material such as a pharmaceutical product. 13 and 14 represent the amplitude and phase at the destination or prior to delivery of the material. The height of each amplitude waveform is influenced by the sample under test resistance 102 and represents conductivity of the solution (the sample under test). The resonant frequency corresponds to zero-phase. Each frequency of the waveform as well as its associated, phase contains information about the dielectric constants of the constituent molecules in the solution (the sample under test). These can be discriminated by exposing the solution in the container (the sample under test) with various in frequencies. As an example, these frequencies can vary between, but are not limited to, 10 KHz and 100 MHz. The element 105 which in this example is an inductor can be varied so that the resonant frequency foils within these frequencies. Using a frequency synthesizer of sufficient resolution, such as the Analog Devices AD9954, the frequencies can be varied by 0.1 Hz in a range of a few kilohertz to several megahertz. The analog to digital (A/D) converter 109 may be, for example, but is not limited to, a 24 bit converter. A representative example of a suitable A/D converter could be the Texas Instruments ADS1675.

In another embodiment of the present invention element 105 may be absent or shorted. The combinations of the elements 101, 102, 103, 104 and 111 create a band-pass filter whose amplitude and phase information changes based on the variations of these elements. The signal processing would be similar to the description previously provided herein, although the shapes of the amplitudes and phases would be different.

Figure 1A:
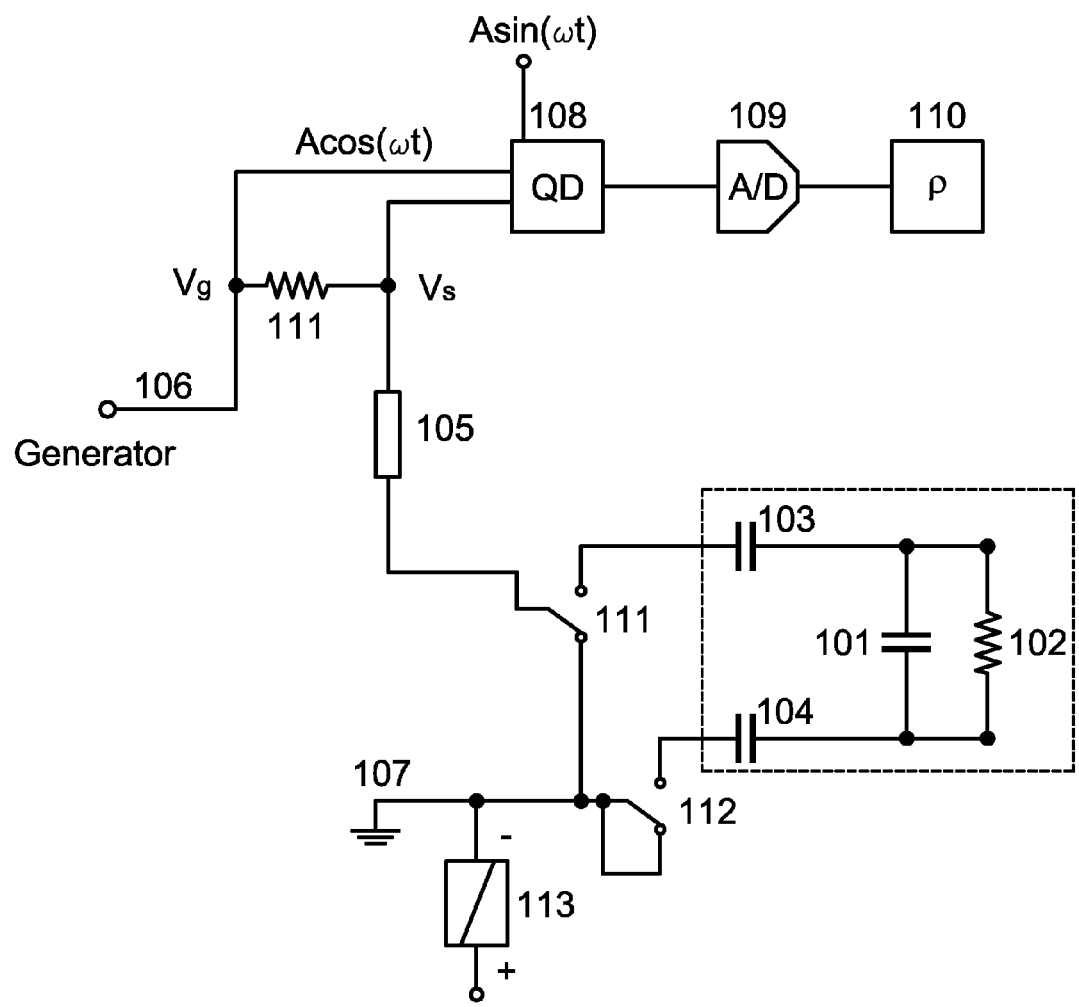
FIG. 1a is a schematic diagram of a further embodiment of the present invention.

FIG. 1A depicts a schematic diagram of a further embodiment of the present invention.

$V_g$ represents a Generator that generates a Cosine wave whose frequency can be varied from approximately 10 KHz-100 MHz with a frequency resolution of 1 Hertz. In some embodiments of the present invention, a precise voltage reference controls the amplitude of this Generator. A separate Generator provides a Sine wave or quadrature demodulation as shown. Resistor 111 is a precise resistance, nominally 1 Kilohm, which is stable with respect to changes in temperature and time. The voltage $V_s$ is a sensed voltage that varies with sample properties. In some embodiment of the present invention, element 105 is an inductor which can be switched between various values, for resonating impedance of the sample. Switch assembly 111, 112, 113 is a low capacitance RF relay that connect the inductor to the sample or to ground for calibration, or to the sample for measurements. The upper relay contacts 111 and lower relay contacts 112 can be seen along with the control gate 113 for activation of the upper relay contacts 111 and lower relay contacts 112. The Quadrature demodulator 108 is a lock in amplifier that generates in-phase and quadrature data based on the difference between $V_g$ at $V_s$. This data is then used in subsequent methods of the present invention related to resonant electrical impulse spectroscopy. The A/D converter 109 is a high resolution converter that, in one embodiment of the present invention, has a resolution of 20-24 Bits and converts the in-phase and quadrature data to amplitude and phase which are the resonant electrical impulse spectroscopy waveforms. The dashed line around 101, 102, 103 and 104 represents the sample under test or an electrical phantom for verifying calibration. Container capacitance 103 and container capacitance 104 represent the capacitance of the walls of the sample holder (such as a glass or plastic container), and may be represented in a circuit as $C_c=(C_{103} \times C_{104})/(C_{103}+C_{104})$ where $C_c$ represents the capacitance of the container that holds the sample under test. $C_{101}$ represents the bulk capacitance of the sample under test and $R_s$ represents resistance of the sample under test due to ionic conductivity.

To ensure proper calibration, inductors used in this system of the present invention are a few millihenries and are made with high frequency ferrites. The permeability of ferrites as well as the resistance of the inductor can vary with temperature and time. The position of switch assembly 111, 112, 113 depicted in FIG. 1A is for calibration. To calibrate the inductor, the generator $V_g$ is swept around the 3 dB point of the low pass filter formed by resistor 111 and inductor (element) 105 and the phase and demodulated signals are then used for calculating changes in the inductor. Initially a one-time calibration is performed for the inductor and its value is stored in memory of the processor, as L. If the measured value of the inductor is $L_m$ the frequencies of the resonant electrical impulse spectroscopy signal are modified by multiplying them by the square root of $L/L_m$.

In FIG. 2, signatures (curves) 11 and 12 are obtained at the original source of the solution and represent the conditions before the material (i.e., solution in a vial) is shipped to the destination. Therefore, 11 and 12 are essentially the control signatures to be used for baseline comparison with field signatures. The temperature of the container is taken along with these control signatures, and may, in some embodiments of the present invention, include multiple temperature readings each with at least one control signature. A database is then created that contains various perturbations of curves 11 and 12 at various temperatures and contains curves within the usable range of the solution or drug in the container (the sample under test). Ibis database may also contain representative data that includes variations in these curves (signatures) that indicates when a solution (the sample under test) is unusable, for example, when a drug expires. The container for the solution or vial may, in some embodiments of the present invention, be tagged with a unique identification number. This data may be transmitted or used locally at the destination or may, in some embodiments of the present invention, resides on a device attached to a network ("the cloud").

At the destination or point of use, the solution in the container, prior to use, can be measured and curves 13 and 14 created. An identification tag generated at the source will then be used to identify, within a stored database, normal templates for the solution or drug at the temperature of measurement. If necessary the temperature could be changed by measured heating and cooling parameters. Another embodiment of the present invention may include a heater or a cooler such as, for example, a Peltier cooler or warmer in order to bring the solution or drug to the temperature of use. The curves 13 and 14 are then compared to the database for variations within the normal values indicated by 11 and 12, and to determine if the curves 13 and 14 are within these acceptable values at the measured temperature. If the measurements are within normal values, there will be an indication to the operator that this solution is usable. This indication may be an audible tone or a display that may be as simple, as, but not limited to a green and red LED indicator light.

Figure 3:
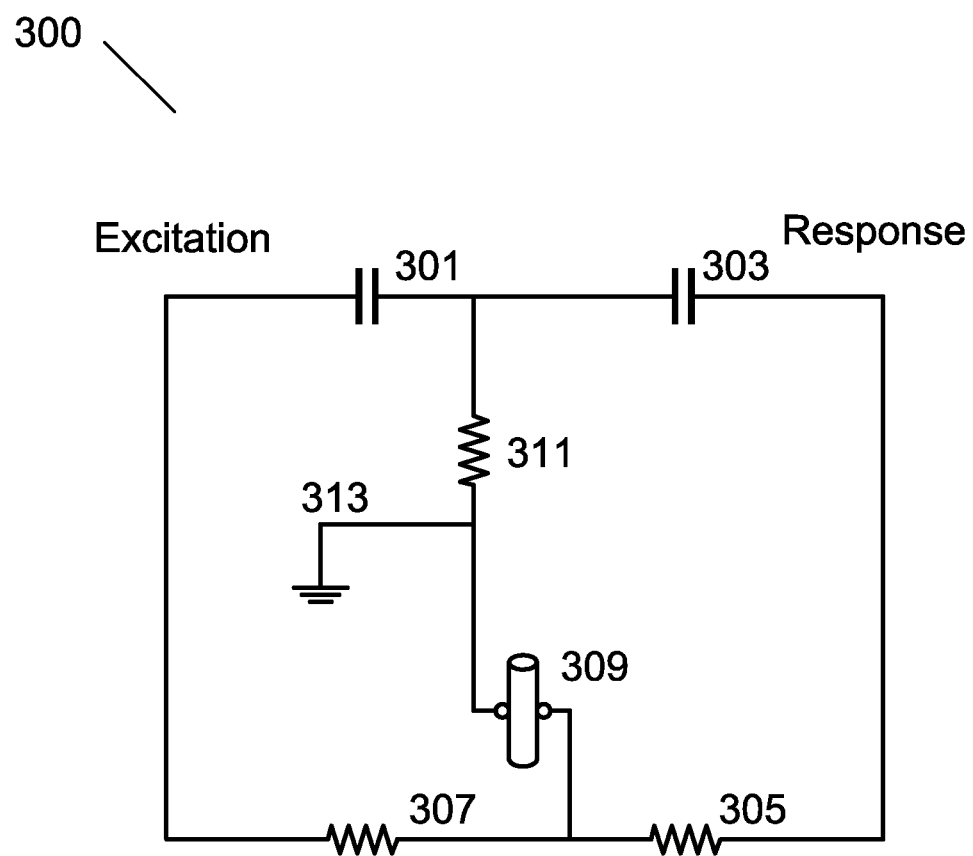
FIG. 3 is a schematic diagram of a twin T notch filter and sample under test of the present invention.

In another embodiment of the present invention, the sample under test could be an element of a Twin-T notch filter, as further depicted by way of FIG. 3. The sample under test 309 can be seen as part of the circuit depicted, with appropriate electrical contacts, such as, for example, electrodes, placed on the sample under test. In some embodiments of the present invention, the electrical contacts are electrodes that make physical contact with, or are in close proximity to, the glass of a container of vial that contains a liquid to be analyzed. The Excitation may be as voltage source or a current source and, in some embodiments of the present invention, phase sensitive demodulation of the Response may be used to create resulting amplitude and phase waveforms at various frequencies The Twin-T notch filter depicted in FIG. 3 employs passive R-C components including a first capacitor 301, a second capacitor 303, a first resistor 305, a second resistor 307 and a third resistor 311. Other components may also be employed to accomplish the functionality of a notch filter, a band reject, or band elimination filter. The component values for the R-C components are determined through calculations or other similar techniques known to those skilled in the art. The twin-T notch filter is used to provide large changes in resonant frequency with small changes in capacitance. The sample under test 309, as stated previously, is electrically connected to this circuit with appropriate electrical contacts.

Sensing elements employed around the material wider test such as around a vial or container are typically capacitive elements. These capacitive elements can be inert materials, such as stainless steel, or in some embodiments of the present invention each of these elements may be made up of bimetals such as those used in thermocouples. These thermocouples may be used to monitor temperature of the elements or in another embodiment of the present invention they may be used as Peltier elements to heat or cool the sample under test.

The present invention may also be used when a plurality of samples under test such as a plurality of vials need to be monitored. In one embodiment of the present invention, a common set of electronics may be used with multiplexers to connect to each of the samples (such as vials).

A microbalance may also be incorporated in another embodiment of the present invention to determine loss of solution during, transport or to determine the density of a powder.

The present invention may also be used to monitor various components such as external resistors, capacitors and inductors, using suitable monitoring circuits. The value of these elements at various times can be used to calibrate the system so that changes in frequency, amplitude and phase of the resulting waveforms can be compensated for the various changes in these elements with time. Fine control of frequency can be achieved, for example, with frequency synthesizers fed by clocks that have jitter of less than 1 pS RMS. In some embodiments of the present invention, the use of signal averaging along with calibrated 24 bit converters will allow changes in amplitude of less than 1/16 ppm as well as frequency changes of a fraction of a Hertz to be determined at a given temperature in order to determine the authenticity as well as the viability of a sample under test.

Applications of the present invention and the various embodiments described, and envisioned herein are numerous and varied. Some examples of uses include in situ use within an organization when transporting a single or as multiplicity of samples under test (containers or vials for example). Other uses include the use of the device, system and method of the present invention within a compounding pharmacy to monitor samples such as containers and vials containing pharmaceuticals for proper chemistry as well as detection of particulate contaminants as well as counterfeiting. Other uses include monitoring during infusion in order to ensure that the correct drug combination is being infused to a patient. In the cosmetics industry, the present invention will determine the authenticity of a cosmetic product between manufacture and transport.

The material signature detector circuit of the present invention can be incorporated in a device such as the material signature detector depicted in FIGS. 4-16 where electrodes are used to facilitate electrical contact with the sample under test. In FIGS. 1 and 1A, the electrodes are operatively connected to each of the two leads going to the sample under test (the representative circuit within the dashed box in both FIGS. 1 and 1A).

Figure 4:
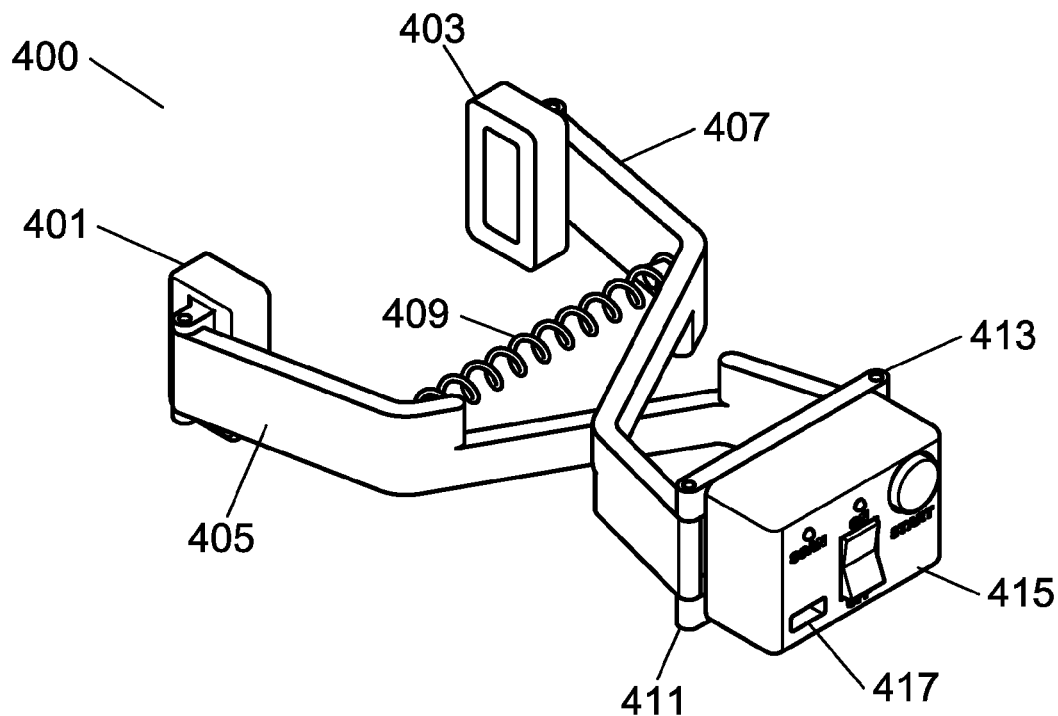
FIG. 4 is a perspective view of the material signature detector of the present invention.

Now with reference to FIG. 4, a perspective view of the material signature detector 400 of the present invention is depicted. The electronics described by way of FIGS. 1, 1A and 3 are contained within the electronics housing 415, which may be made of a plastic, a metal, or the like. As evident in FIG. 4, various interfaces can be seen, such as, for example, an on/off switch, a start button, indicator lights that provide a visual indicator of a scan in progress or the like. In addition, a connector 417 such as a data connector, for example, a USB connector, can be seen. The purpose of the connector 417 is to allow data that has been collected by the material signature detector to be transferred to another device such as a laptop computer, a storage device, a tablet computer, a smartphone, or the like. In addition, a power connector is used to charge batteries (not shown) used to power the device. The connector 417 may be used for that purpose, or a separate power connector may be used. A first electrode 401 and a second electrode 403 can be seen attached to a first arm 405 and a second arm 407 respectively. An electrical connection such as a wire or a cable (not seen in FIG. 4) runs from each electrode to the electronics housing 415 where it terminates at the material signature detector circuit contained within the electronics housing 415. The way in which the electrodes are connected to the material signature detector circuit is evident from FIGS. 1, 1A and 3 and the related description of these figures. The first arm 405 and the second arm 407 are formed in a scissors or tongs like configuration to facilitate contact with a sample under test. A spring 409 spans the first arm 405 and the second arm 407 to provide a return force to the arrangement such that the electrodes are seated firmly on the sample under test. The first arm 405 and the second arm 407 may also be cut way along the area where they cross each other to facilitate an adequate range of motion. In addition, the first arm 405 and the second arm 407 are hinged to the electronics housing with a first hinge 411 and a second hinge 413. The first arm 405 and the second arm 407, along with the first hinge 411 and the second hinge 413 may be made from a plastic or a metal. To use the material signature detector, the first arm 405 and the second arm 407 are separated and a sample under test is placed such that the first electrode 401 contacts one side of the sample under test and the second electrode 403 contacts the other side of the sample under test such that the sample under test appears as a circuit element as previously described.

Figure 5:
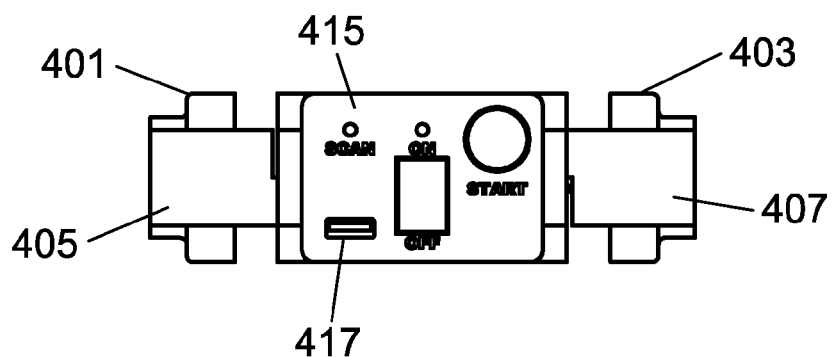
FIG. 5 is a from plan view of the material signature detector of the present invention.

FIG. 5 is a front plan view of the material signature detector of the present invention where the exemplary interface can be seen. In some embodiments of the present invention, the interface may be a display screen, a touch screen, or the like.

Figure 6:
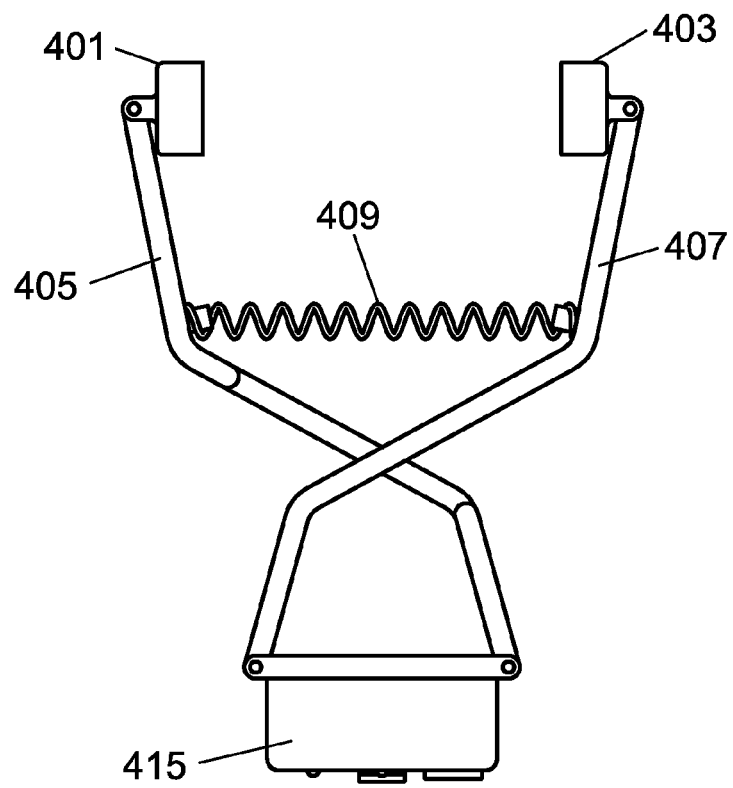
FIG. 6 is a top plan view of the material signature detector of the present invention.
Figure 7:
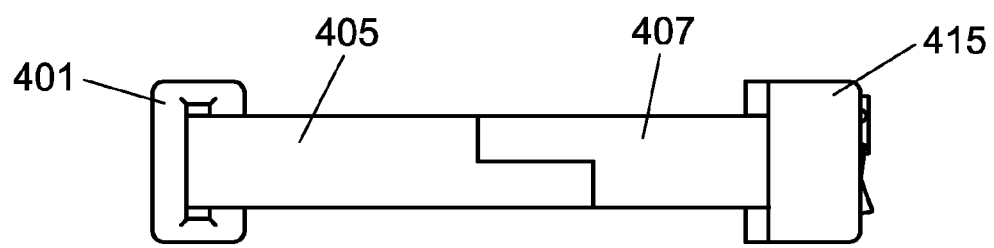
FIG. 7 is a left side plan view of the material signature detector of the present invention.
Figure 8:
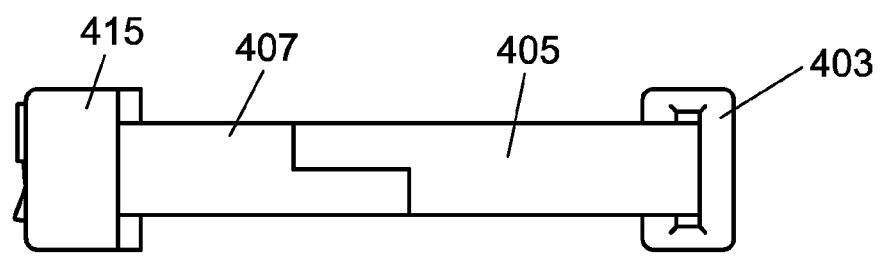
FIG. 8 is as right side plan view of the material signature detector of the present invention.

FIG. 6 is a top plan view of the material signature detector of the present invention. FIG. 7 is a left side plan view of the material signature detector of the present invention, and FIG. 8 is a right side plan view of the material signature detector of the present invention. The mechanism to attach the electrodes to the sample under test can be clearly seen.

Figure 9:
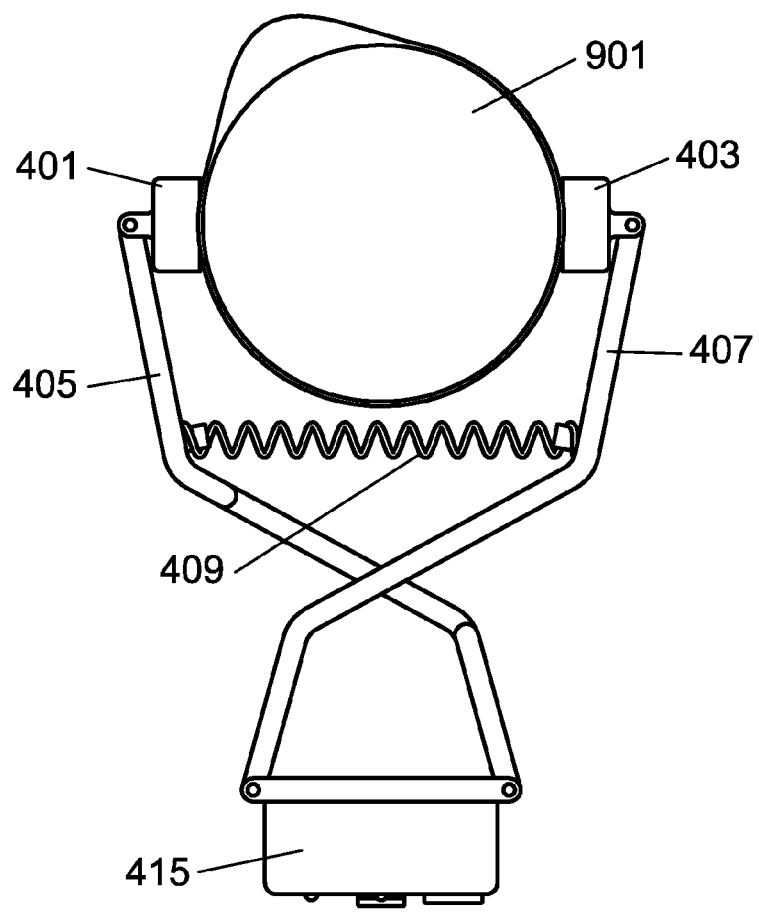
FIG. 9 is a top plan view of the material signature detector of the present invention in use with a beaker of material.
Figure 10:
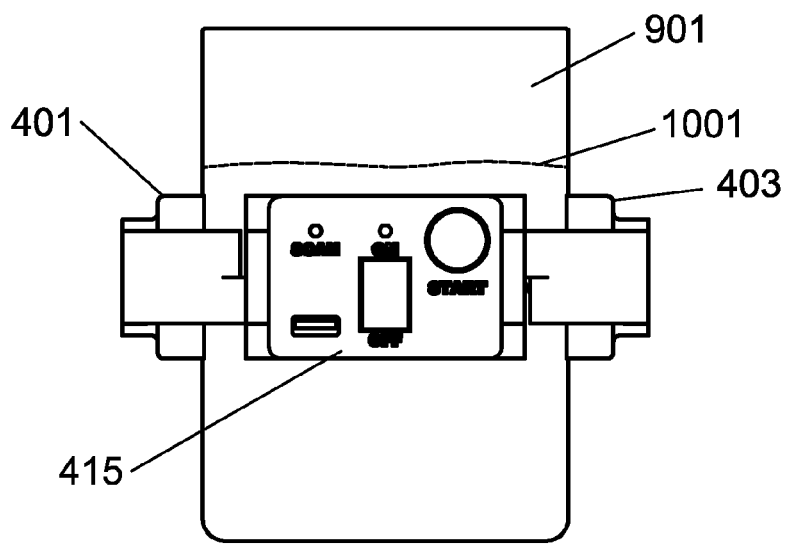
FIG. 10 is a front plan view of the material signature detector of the present invention in use with a beaker of material.
Figure 11:
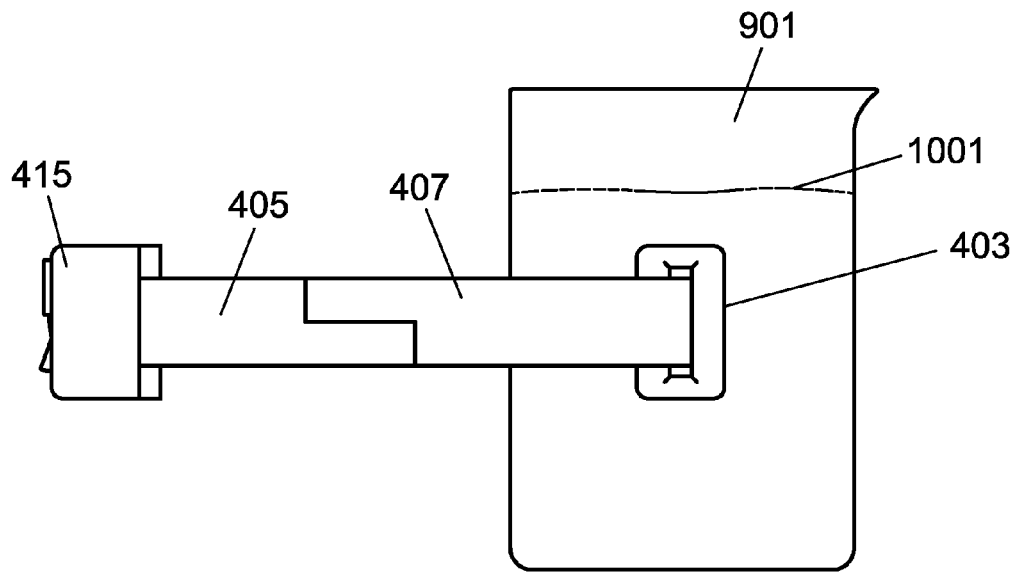
FIG. 11 is a left side plan view of the material signature detector of the present invention in use with a beaker of material.
Figure 12:
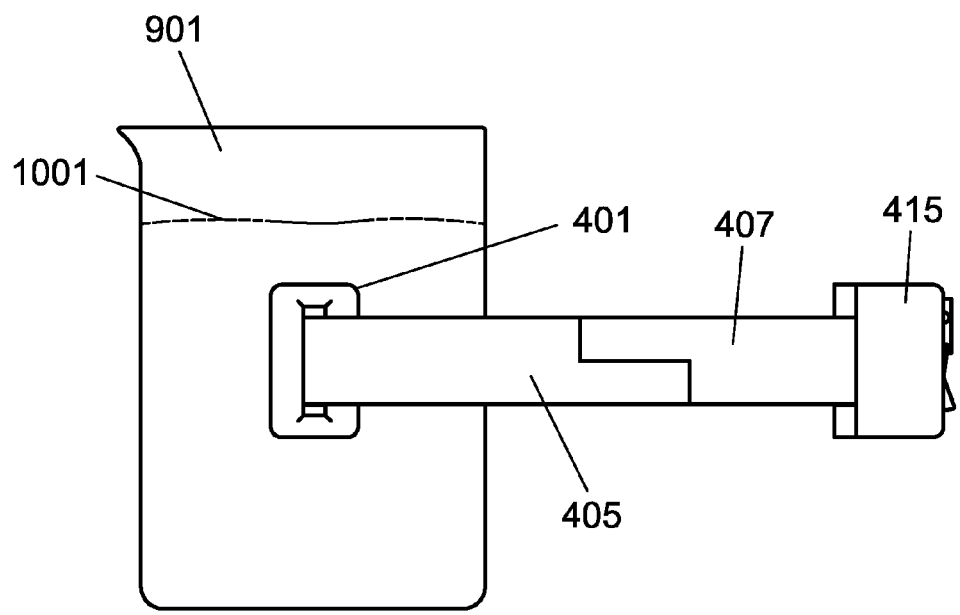
FIG. 12 is a right side plan view of the material signature detector of the present invention in use with a beaker of material.
Figure 13:
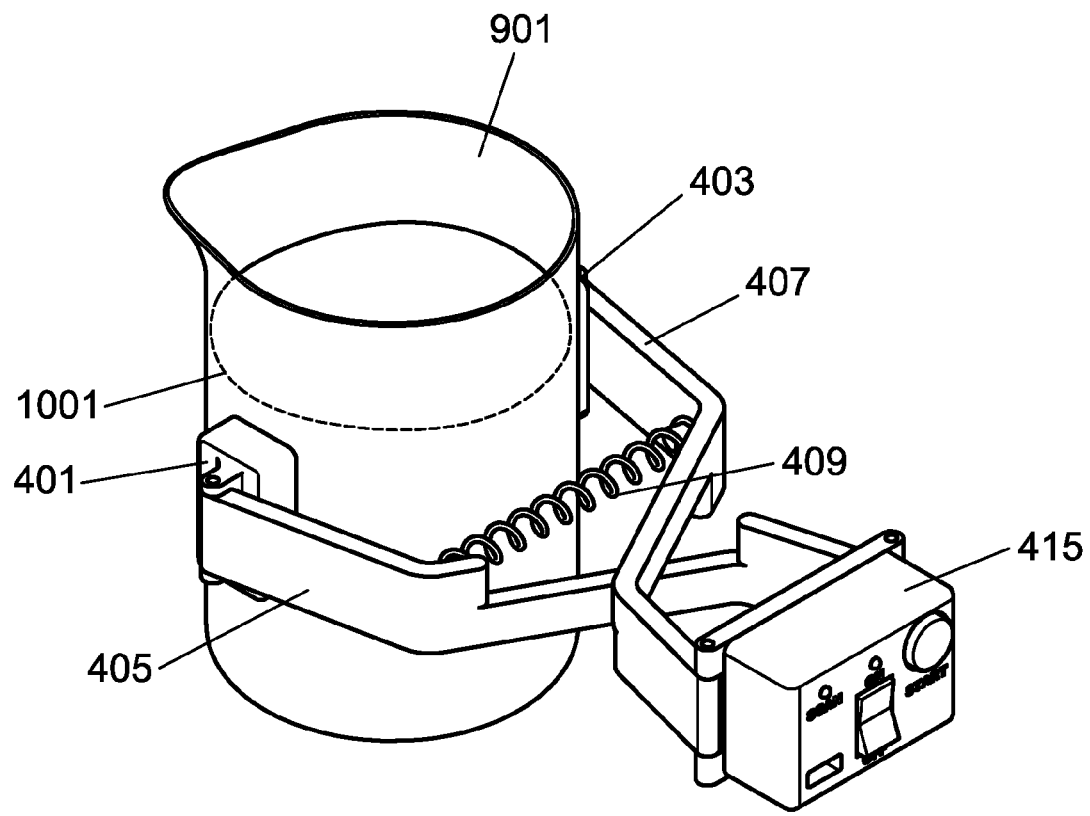
FIG. 13 is a perspective view of the material signature detector of the present invention in use with a beaker of material.

FIG. 9 is a top plan view of the material signature detector of the present invention in use with a beaker of material 901. The expandable nature of the material signature detector can be clearly seen as well as exemplary positioning of the electrodes on the beaker of material 901. As stated previously, each side of the glass from the beaker appears electrically as a capacitor and the material within the beaker appears electrically as a resistor in parallel with a capacitor. FIG. 10 is a front plan view the signature detector of the present invention in use with a beaker of material where the conductive or transmissive path of the signal between the first electrode 401 and the second electrode 403 can be seen. The material under test 1001 can be seen within the beaker, and may be a liquid or a powder, for example. FIG. 11 is as left side plan view of the material signature detector of the present invention in use with a beaker of material. FIG. 12 is a right side plan view of the material signature detector of the present invention in use with a beaker of material. FIG. 13 is a perspective view of the material signature detect the p sent invention in use with a beaker of material.

FIG. 14 is a top plan view of the material signature detector of the present invention in use with a vial of material 1401. The expandable nature of the material signature detector can be clearly seen. FIG. 15 is a front plan view of the material signature detector of the present invention in use with a vial 1401 containing material under test 1501.

Figure 16:
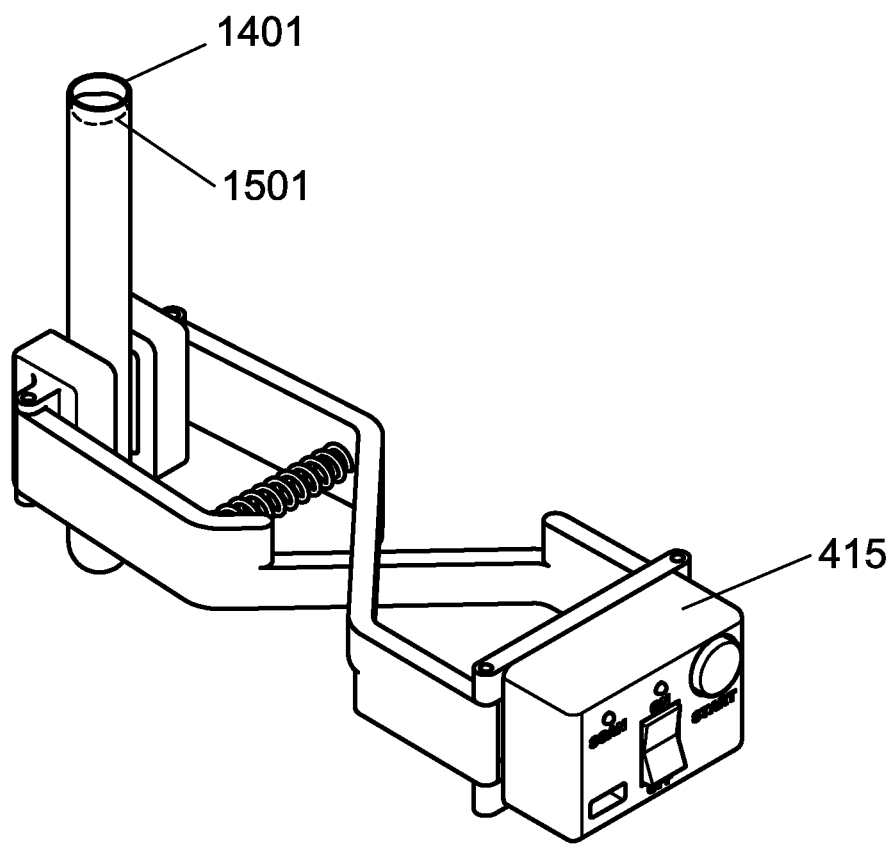
FIG. 16 is a perspective view of the material signature detector of the present invention in use with a vial of material.

Lastly, FIG. 16 is a perspective view of the material signature detector of the present invention in use with a vial 1401 containing material under test 1501.

The present invention also includes methods for non-contact assessment of changes in critical material properties. These methods may be performed manually, or they may be automated or otherwise made part of a software program residing on as processor with related memory. A method of the present invention comprises the steps of placing as sample under test in a series circuit with a sense resistor and an element, as more clearly seen in FIGS. 1, 1A and 3, applying a signal between the sense resistor and a ground return, demodulating the signal across the sense resistor using as quadrature demodulator, receiving the demodulated analog signal from the quadrature demodulator with an analog to digital converter; converting with the analog to digital converter the demodulated analog signal to a digital signature that is indicative of material properties of the sample under test. The digital signature may also be stored or otherwise retained for future use, such as the creation of a library of digital signatures that are used to determine the properties of a material under test. This method of the present invention may also further comprise the steps of changing the frequency of the signal applied between the sense resistor and ground return, demodulating the signal across the sense resistor using a quadrature demodulator, receiving the demodulated analog signal from the quadrature demodulator with an analog to digital converter, converting with the analog to digital converter the demodulated analog signal to another digital signature that is further indicative of material properties of the sample under test. These additional steps may be repeated multiple times at different frequencies, thus creating a signature spectrum of sorts that may be further used for identifying material properties of a sample under test.

This method of the present invention may also include the steps of collecting the created digital signatures in a data storage device and associating the collected digital signatures with material properties.

In addition, in some embodiments of the present invention, the signal applied between the sense resistor and the ground return is in the range of 10 kilohertz and 100 megahertz.

The collected digital signatures comprise amplitude and phase information, and may include as series of digital signatures taken at varying frequencies. The frequency may be varied in increments such as 0.1 hertz increments, or larger increments depending on the requirements of the analysis of material properties to be performed.

It is, therefore, apparent that there has been provided, in accordance with the various objects of the present invention, a System and Method For Non-Contact Assessment of Changes in Critical Material Properties. While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the present invention as defined by this specification and the attached drawings and claims.

What is claimed is:

1. A material signature detector for non-contact assessment of changes in critical material properties comprising:
    an electrical circuit comprising a sense resistor in series with both an element and a sample under test;
    a frequency source electrically coupled between the sense resistor and a ground return;
    a quadrature demodulator electrically coupled to the sense resistor; and
    an analog to digital converter to create digital signatures from analog signals received from the quadrature demodulator;
    a computer having a processor, memory, and access to computer readable media;
    the computer configured to receive the created digital signatures;
    a computer program stored on the computer readable media where the computer program executes the steps of:
    applying a signal between the sense resistor and a ground return;
    demodulating the signal across the sense resistor using a quadrature demodulator;
    receiving the demodulated analog signal from the quadrature demodulator with an analog to digital converter;
    converting with the analog to digital converter the demodulated analog signal to a digital signature that is indicative of material properties of the sample under test;
    changing the impedance value of the element;
    applying a signal between the sense resistor and a ground return;
    demodulating the signal across the sense resistor using a quadrature demodulator;
    receiving the demodulated analog signal from the quadrature demodulator with an analog to digital converter;
    converting with the analog to digital converter the demodulated analog signal to another digital signature that is further indicative of material properties of the sample under test.

2. The material signature detector of claim 1, wherein the sample under test comprises a material within a container.

3. The material signature detector of claim 2, wherein the material of the sample under test has an impedance.

4. The material signature detector of claim 1, wherein the container of the sample under test has a container capacitance.

5. The material signature detector of claim 1, wherein the element is an inductor.

6. The material signature detector of claim 1, wherein the frequency source produces frequencies in the range of 10 Kilohertz to 100 Megahertz.

7. The material signature detector of claim 1, further comprising a peltier device for heating or cooling the sample under test.

8. The material signature detector of claim 1, further comprising a microbalance to determine weight of the sample under test.

9. The material signature detector of claim 1, further comprising a twin T notch filter with the sample under test used as an element of the twin T notch filter such that small changes in capacitance result in large changes in resonant frequency.

10. A method for non-contact assessment of changes in critical material properties, the method comprising the steps of:

placing a sample under test in a series circuit with a sense resistor and an element;
applying a signal between the sense resistor and a ground return;
demodulating the signal across the sense resistor using a quadrature demodulator;
receiving the demodulated analog signal from the quadrature demodulator with an analog to digital converter;
converting with the analog to digital converter the demodulated analog signal to a digital signature that is indicative of material properties of the sample under test;
changing the impedance value of the element;
applying a signal between the sense resistor and a ground return;
demodulating the signal across the sense resistor using a quadrature demodulator;
receiving the demodulated analog signal from the quadrature demodulator with an analog to digital converter;
converting with the analog to digital converter the demodulated analog signal to another digital signature that is further indicative of material properties of the sample under test.

11. The method as recited in claim 10, further comprising the steps of:
changing the frequency of the signal applied between the sense resistor and ground return;
demodulating the signal across the sense resistor using a quadrature demodulator;
receiving the demodulated analog signal from the quadrature demodulator with an analog to digital converter;
converting with the analog to digital converter the demodulated analog signal to another digital signature that is further indicative of material properties of the sample under test.

12. The method as recited in claim 11, further comprising the steps of:
collecting the created digital signatures in a data storage device; and
associating the collected digital signatures with material properties.

13. The method as recited in claim 10, wherein the digital signature comprises amplitude and phase information.

* * * * *